(12) United States Patent
Mayer

(10) Patent No.: US 9,874,520 B1
(45) Date of Patent: Jan. 23, 2018

(54) EPI-FLUORESENCE CONFOCAL OPTICAL ANALYTE SENSOR

(71) Applicant: MOCON, INC., Minneapolis, MN (US)

(72) Inventor: Daniel W. Mayer, Wyoming, MN (US)

(73) Assignee: MOCON, INC., Minneapolis, MN (US)

( * ) Notice: Subject to any disclaimer, the term of this patent is extended or adjusted under 35 U.S.C. 154(b) by 0 days.

(21) Appl. No.: 14/972,233

(22) Filed: Dec. 17, 2015

Related U.S. Application Data

(63) Continuation of application No. 12/614,705, filed on Nov. 9, 2009, now abandoned.

(60) Provisional application No. 61/112,547, filed on Nov. 7, 2008.

(51) Int. Cl.
*G01J 1/58* (2006.01)
*G01N 21/64* (2006.01)

(52) U.S. Cl.
CPC ......... *G01N 21/645* (2013.01); *G01N 21/643* (2013.01); *G01N 21/6408* (2013.01); *G01N 2021/6432* (2013.01); *G01N 2201/068* (2013.01); *G01N 2201/12* (2013.01)

(58) Field of Classification Search
CPC ................................................. G01N 21/6428
See application file for complete search history.

(56) References Cited

U.S. PATENT DOCUMENTS

| 4,476,870 A | 10/1984 | Peterson et al. |
| 4,810,655 A | 3/1989 | Khalil et al. |
| 5,190,729 A | 3/1993 | Hauenstein et al. |
| 5,382,163 A | 1/1995 | Putnam |
| 5,495,850 A * | 3/1996 | Zuckerman ............ 600/313 |
| 5,718,842 A | 2/1998 | Papkovsky et al. |
| 6,074,607 A | 6/2000 | Slovacek et al. |
| 6,153,701 A | 11/2000 | Potnis et al. |
| 6,266,211 B1 | 7/2001 | Thomas, III et al. |
| 6,379,969 B1 | 4/2002 | Mauza et al. |
| 6,689,438 B2 | 2/2004 | Kennedy et al. |

(Continued)

FOREIGN PATENT DOCUMENTS

WO 20070120637 A2 10/2007

OTHER PUBLICATIONS

Lee, Sang-Kyung et al., "Photoluminescent Oxygen Sensing on a Specific Surface Area Using Phosphorescence Quenching of Pt-Pophyrin", Analitical Sciences, Departament of Bioengineering, Tokyo Institute of Technology, pp. 535-540, Aug. 1997, vol. 13.
Eaton, K. et al., "Effect of Humidity on the Response Characteristics of Luminescent PtOEP Thin Film Optical Oxygen Sensors", Elsevier Science B. V., pp. 94-104, 2002.
Technical Manual, "Freudenberg Grafted Products", Sep. 2006, pp. 1-32.

(Continued)

*Primary Examiner* — David Porta
*Assistant Examiner* — Hugh H Maupin
(74) *Attorney, Agent, or Firm* — Sherrill Law Offices, PLLC

(57) ABSTRACT

An optical sensor effective for (i) exciting an analyte-sensitive fluorophore, exposed to an unknown concentration of the analyte for which the fluorophore is sensitive, with radiant energy from an excitation source, (ii) measuring the extent to which luminescence of the excited fluorophore is quenched by presence of the analyte, (iii) ascertaining the concentration of analyte to which the fluorophore is exposed from such measurement, and (iv) reporting the ascertained concentration. The sensor is preferably an epi-fluroescence confocal optical detector, and preferably performs step (ii) by employing a summing amplifier.

3 Claims, 5 Drawing Sheets

(56) References Cited

U.S. PATENT DOCUMENTS

| | | | |
|---|---|---|---|
| 7,138,270 | B2 | 11/2006 | Papkovsky et al. |
| 7,199,360 | B1 | 4/2007 | Montagu |
| 7,368,153 | B2 | 5/2008 | Barmore et al. |
| 7,534,615 | B2 | 5/2009 | Havens |
| 7,569,395 | B2 | 8/2009 | Havens et al. |
| 2003/0027126 | A1* | 2/2003 | Walt et al. .................. 435/4 |
| 2005/0064427 | A1 | 3/2005 | Gluch et al. |
| 2005/0159497 | A1 | 7/2005 | Gauthier et al. |
| 2006/0002822 | A1 | 1/2006 | Papkovsky et al. |
| 2007/0041011 | A1 | 2/2007 | Hayden et al. |
| 2007/0212792 | A1 | 9/2007 | Havens et al. |
| 2007/0243618 | A1 | 10/2007 | Hatchett et al. |
| 2008/0051646 | A1 | 5/2008 | Claps et al. |
| 2008/0148817 | A1 | 6/2008 | Miller et al. |
| 2008/0190172 | A1 | 8/2008 | Jones |
| 2008/0199360 | A1 | 8/2008 | Shahriari |
| 2008/0215254 | A1 | 9/2008 | Leiner et al. |
| 2008/0242873 | A1 | 10/2008 | Meador et al. |
| 2009/0029402 | A1 | 1/2009 | Papkovsky |
| 2009/0130700 | A1 | 5/2009 | Ince et al. |
| 2010/0209937 | A1 | 8/2010 | Geddes et al. |

OTHER PUBLICATIONS

Papkovsky, D. et al., "Phosphorescent Sensor Aproach for Non-Destructive Measurments of Oxigen in Packaged Foods: Optimisation of Disposable Oxygen Sensors and Their Characterization Over a Wide Temperature Range", Departament of Biochemestry National University of Ireland, Analitical Letters, 33 (9), pp. 1755-1777, 2000.

Austin, Ead et al., "Opto-electronic systems for addressing Ru oxygen sensors: their design optimization and calibration process", Invited Paper, Optoelectronics Research Centre, University of Southampton, Southampton S017 IBJ.

De Francisci, M. et al., "Real-Time Estimation of Oxygen Concentration in Micro-Hemo-Vessels", Proceedings of the 26th Annual International Conference of the IEEE EMBS San Francisco, CA, USA' Sep. 1-5, 2004.

Nguyen, N. Callamaras, C. Hsieh, I. Parker, "Construction of a two-photon microscope for video-rate Ca2+ imaging," Cell Calcium, vol. 30, No. 6 (2001), p. 383-393.

\* cited by examiner

*Fig. 4*

OpTech™-O₂ Platinum

Additional features:

Less sensitive to ambient light
Less affected by temperature changes
On/Off sampling button

Cutting edge software:
Store thousands of data points
Continuously monitor O$_2$
Graph O$_2$% vs time curves
Automatic change of
    database
    screen
    product
    user name
Built in test methods can be linked to product.
Built in temperature and barometric compensation.

Contemporary design:
Fits nicely into either hand.
Rotate in any direction.
Trigger with any finger.
Lightweight.
Simple docking, needle storage station.

| | |
|---|---|
| Sample size | Limited to the size of the platinum sensor |
| Repaetability (Certified) | +/- 0.001% 02 from 0.0001% to 30% 02 |
| Range | 10ppm to 30% 02 |
| Response | 98% of final value within 0.5 seconds |
| Warm-up time | None |
| Resolution | 1ppm in range of 1% to 25% 02 |
| Measurement method | Epifluorence Confocal |
| Sample method | Optical system with on/off button |
| Base dimensions | Width: 4.8"  12.19 cm<br>Height: 2.7"  6.8 cm<br>Depth: 10"  25.40 cm<br>Weight: Approximately 5 pounds, 2.27 kg |
| Optical probe dimensions | Width: 1.3"  3.30 cm<br>Height: 1.9"  4.83 cm<br>Depth: 9" (with needle), 6" (without needle)<br>    22.86 cm    15.24 cm<br>Weight: Approximately 0.5 pounds, 0.23 kg |
| Operating temperature | 5-40C |
| Operating humidity | 0-100% non-condensing |
| Universal power supply | |
| voltage | USB 5V |
| Powersupply wattage | 2.5 watt |
| Compliance | CE/CSA/UL |
| Communications | USB |
| User interfaces | USB ports optional products |
| PDF report options | Thru program ffrom computer |

EPI-FLUORESENCE CONFOCAL OPTICAL ANALYTE SENSOR

BACKGROUND

Optical sensors are a widely employed method of measuring analyte concentration, typically oxygen, within a package or container. Briefly, analyte concentration within a package or container can be measured by placing an analyte sensitive fluorophore within the package or container, allowing the fluorophore to equilibrate within the package or container, exciting the fluorophore with radiant energy, and measuring the intensity and/or rate of decay in the intensity of luminescence emitted by the excited fluorophore. Such optical sensors are available from a number of suppliers, including Presens Precision Sensing, GmbH of Regensburg, Germany.

Optical sensors typically employ fiber optics to both guide the excitation light generated by the sensor from the sensor to the analyte sensitive fluorophore, and also guide emitted light from the fluorophore to a photo multiplier in the optical sensor for detection and measurement.

While effective for accurately measuring analyte concentration, such optical sensors are very expensive.

Accordingly, a substantial need exists for a low cost optical sensor capable of accurately and reliably measuring analyte concentration within a package or container.

SUMMARY OF THE INVENTION

The invention is directed to an optical sensor. A first embodiment of the invention is an epi-fluroescence confocal optical detector effective for (i) exciting an analyte-sensitive fluorophore, exposed to an unknown concentration of the analyte for which the fluorophore is sensitive, with radiant energy from an excitation source, (ii) measuring the extent to which luminescence of the excited fluorophore is quenched by presence of the analyte, (iii) ascertaining the concentration of analyte to which the fluorophore is exposed from such measurement, and (iv) reporting the ascertained concentration.

A second embodiment of the invention is an optical detector effective for (i) exciting an analyte-sensitive fluorophore, exposed to an unknown concentration of the analyte for which the fluorophore is sensitive, with radiant energy from an excitation source, (ii) measuring the extent to which luminescence of the excited fluorophore is quenched by presence of the analyte employing a summing amplifier, (iii) ascertaining the concentration of analyte to which the fluorophore is exposed from such measurement, and (iv) reporting the ascertained concentration.

BRIEF DESCRIPTION OF THE DRAWINGS

FIG. 4 is a specification sheet for an exemplary embodiment of the invention.

DETAILED DESCRIPTION OF A PREFERRED EMBODIMENT

Definitions

As used herein, including the claims, the term "fluorophore" means a molecule with a functional group which can absorb energy of a specific wavelength and as a result emit energy at a different specific wavelength (i.e., a fluorescent molecule).

As used herein, including the claims, the phrase "analyte sensitive fluorophore" means a fluorophore whose level of fluorescence changes upon exposure to a specific analyte (e.g., oxygen) in proportion to the amount of analyte.

Nomenclature

10 Optical Detection Unit
15 Housing for Optical Detection Unit
20 Source of Excitation Light
30 Dichroic Mirror
40 Pinhole
50 Photo Detector
60 Docking Station for Optical Detection Unit
100 Analyte-Sensitive Fluorophore
200 Container
210 Chamber of Container
A Excitation Light
B Emitted Light

Construction

Figure 1:
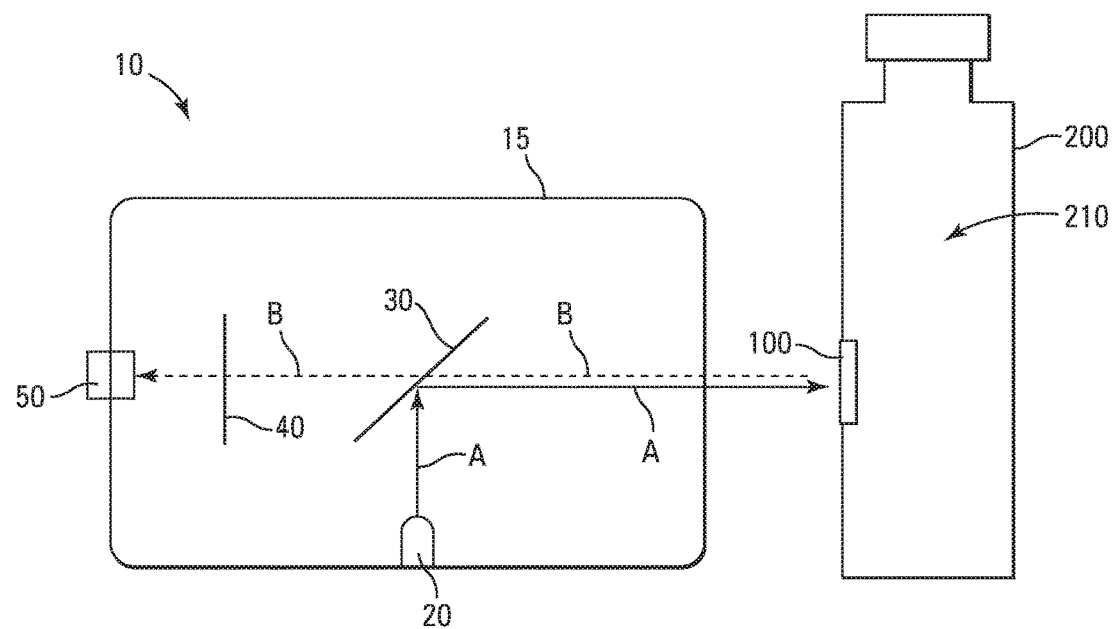
FIG. 1 is a schematic view of one embodiment of the invention.
Figure 2:
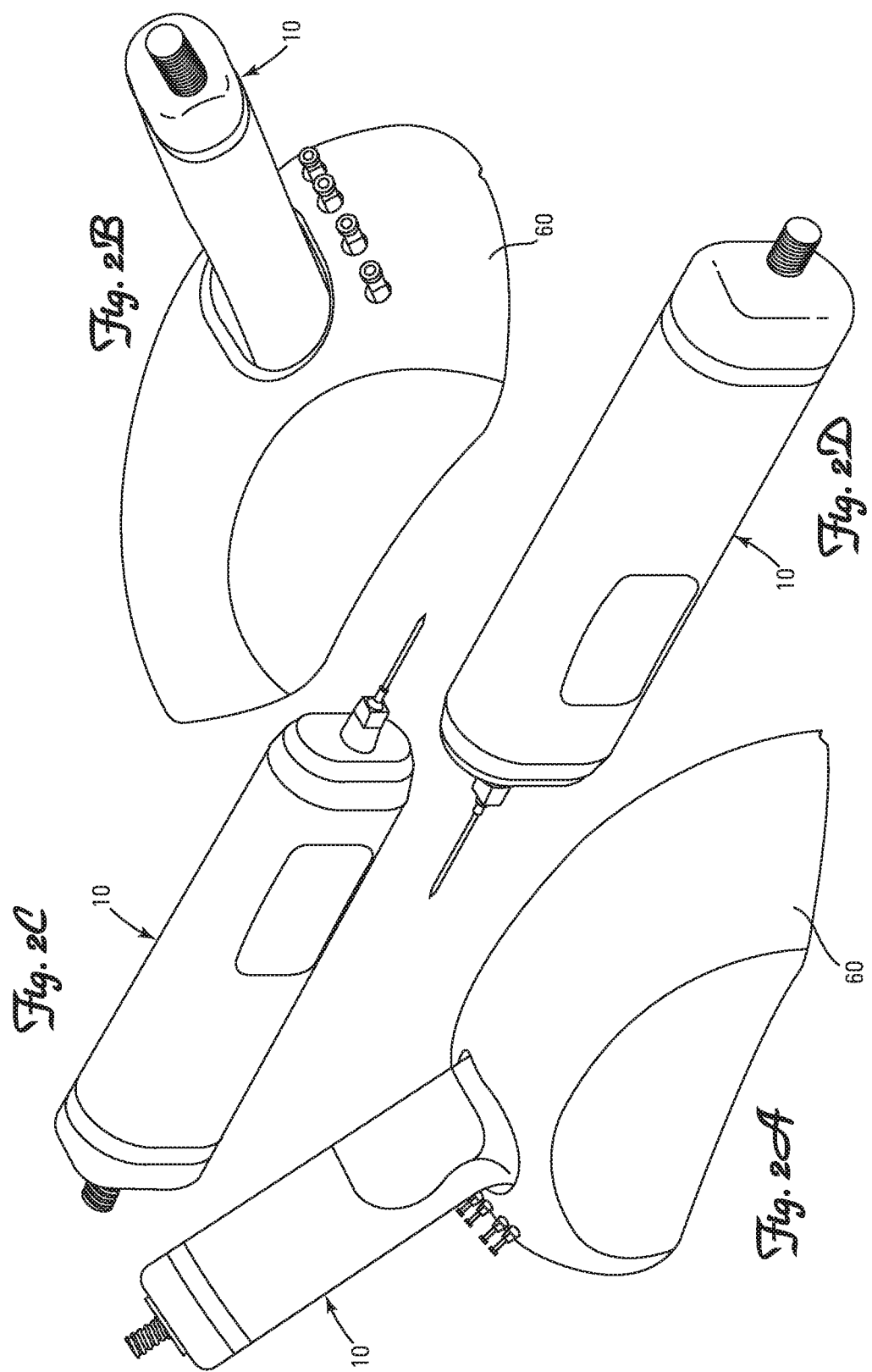
FIG. 2A is front perspective view of one embodiment of the invention.
FIG. 2B is rear perspective view of the invention depicted in FIG. 2A.
FIG. 2C is front perspective view of the handheld detector portion of the invention depicted in FIGS. 2A and 2B.
FIG. 2D is rear perspective view of the handheld detector portion of the invention depicted in FIGS. 2A and 2B.
Figure 3:
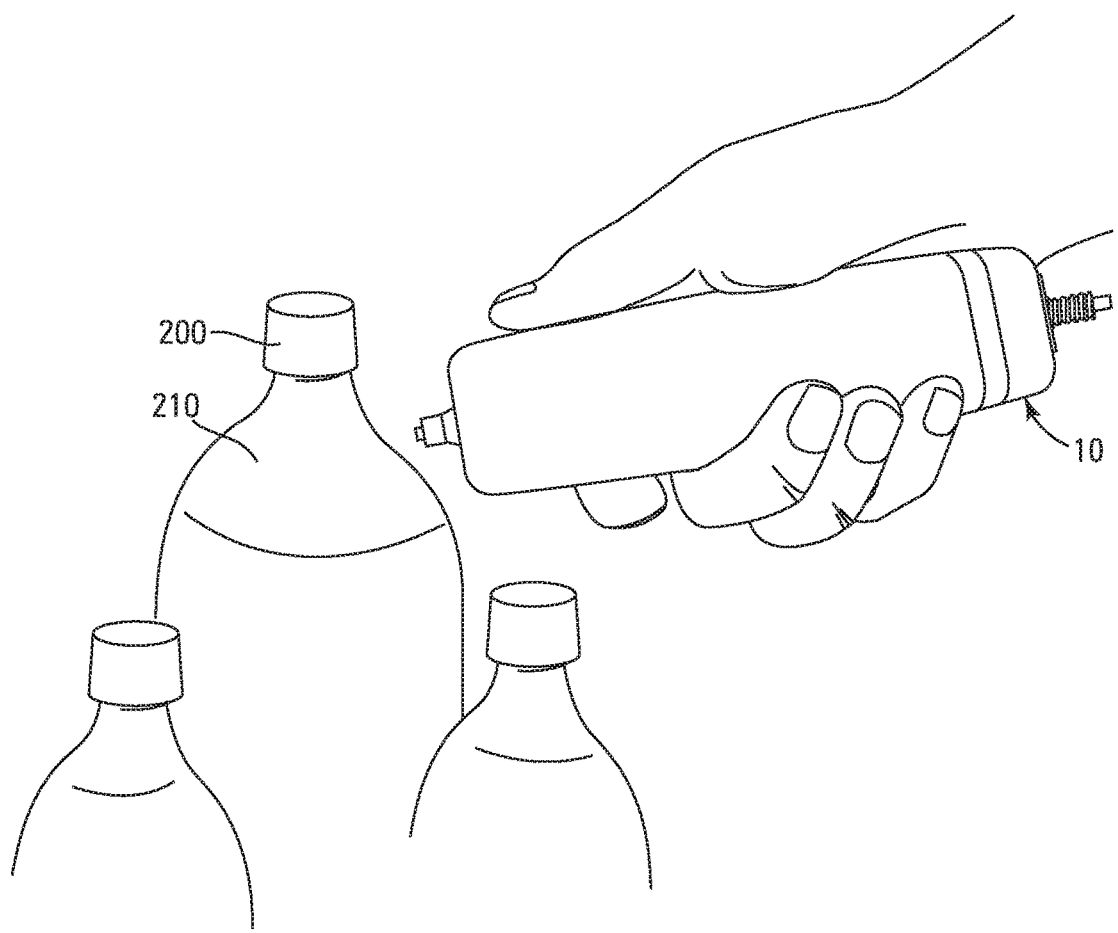
FIG. 3 depicts usage of the handheld detector portion of the invention depicted in FIGS. 2A-D to detect the oxygen concentration within a bottle containing a carbonated beverage.
Figure 5:
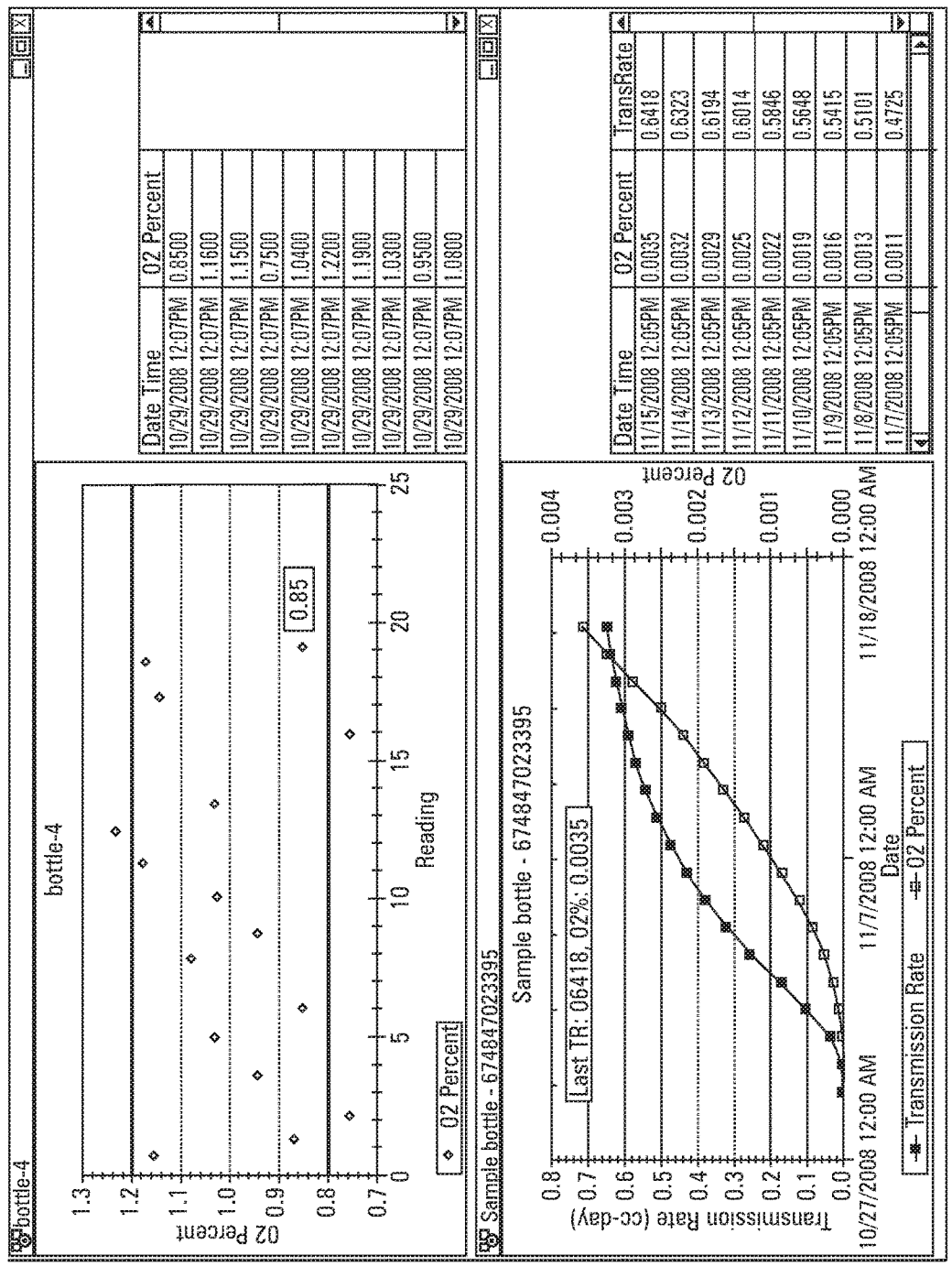
FIG. 5 is a depiction of an exemplary report of oxygen percentage and transmission rate for a sample bottle.

Referring generally to FIG. 1, the invention is an optical sensor, comprising an epi-fluroescence confocal optical detector 10 for detecting the intensity of light emitted by an analyte-sensitive fluorophore 100 exposed to an unknown concentration of the analyte, ascertaining a concentration of analyte from a phase shift in the detected intensity and reporting the ascertained concentration.

The optical detection unit 10 includes a source 20 of excitation light A that is reflected by a dichroic mirror 30 towards an opening (unnumbered) through the housing 15. The excitation light A is absorbed by an analyte-sensitive fluorophore 100 such as a platinum based fluorophore dot 100 placed within the chamber 210 of a MAP container 200. Emitted light B from the fluorophore 100 returns back through the opening (unnumbered) in the housing 15, passes through the dichroic mirror 30, passes through a confocal pinhole 40 and is detected by a photo detector 50.

A docking station 60 may be provided for the optical detection unit 10 for facilitating electrical connection of the optical detection unit 10 with a computer (not shown) or other electronics.

The photo detector 50 includes a summing amplifier and is capable of receiving emitted light B over an extended period of time during which the fluorophore 100 emitting the emitted light B receives a plurality of pulses of excitation light A from the source 20 of excitation light A. The photo detector 50 is able to ascertain the rate at which the intensity of the emitted light B decays, and delivers an output signal proportional to the ascertained rate of decay. The output signal from the photo detector 50 is converted by a microprocessor (not shown) to a concentration of analyte employing a lookup table and/or an algorithm, and the ascertained concentration reported.

Various analyte sensitive fluorophores are known and widely available from a number of sources, including Sigma-Aldrich of St. Louis, Mo. For example, a family of ruthenium-based oxygen sensitive luminescence indicator compositions are disclosed and described in WO 2007/120637. A preferred fluorophore is platinum porphyrin. The benefits of employing platinum porphyrin rather than a ruthenium-based compound as the oxygen sensitive luminescence indicator include (i) less sensitivity to ambient light, (ii) ability to excite at wavelengths other than ultraviolet, (iii) increased sensitivity, and (iv) a longer decay period.

I claim:

1. A method of measuring the concentration of an analyte in packaging, comprising the steps of:
   (a) identifying a hermetically sealed package retaining a product within a payload retention chamber, the package equipped with a probe bearing an analyte-sensitive fluorophore element in analyte sensing communication with the payload retention chamber of the package,
   (b) exposing the analyte-sensitive fluorophore element to excitation radiation,
   (c) measuring radiation emitted by the excited analyte-sensitive fluorophore element using a photo detector, wherein a confocal element is positioned between the analyte-sensitive fluorophore element and the photo detector so that only light emitted from a limited area on the excited analyte-sensitive fluorophore reaches the photo detector, and
   (d) converting the measured emission from a limited area on the excited analyte-sensitive fluorophore to an analyte concentration based upon a known conversion algorithm, and
   (e) displaying the ascertained concentration.

2. The method of claim 1 wherein the analyte is oxygen.

3. The method of claim 1 wherein the step of converting measured emission to an analyte concentration employs a time resolved fluorescence approach.

* * * * *